United States Patent [19]

Smith

[11] 4,035,408

[45] July 12, 1977

[54] PROCESS FOR HYDROFORMYLATION OF ALLYL ACETATE OR 1-PROPENYL ACETATE

[75] Inventor: William E. Smith, Schenectady, N.Y.

[73] Assignee: General Electric Company, Schenectady, N.Y.

[21] Appl. No.: 632,482

[22] Filed: Nov. 17, 1975

Related U.S. Application Data

[62] Division of Ser. No. 548,216, Feb. 10, 1975, Pat. No. 3,941,851, which is a division of Ser. No. 371,929, June 20, 1973, Pat. No. 3,880,913.

[51] Int. Cl.$^2$ ............................................ C07C 67/28
[52] U.S. Cl. ............................ 260/491; 260/497 A; 260/541; 260/601 R; 260/635 A; 260/635 R

[58] Field of Search ..................................... 260/491

[56] References Cited

U.S. PATENT DOCUMENTS

| 3,239,569 | 3/1966 | Slaugh et al. | 260/491 |
| 3,661,980 | 5/1972 | Himmele et al. | 260/491 |

Primary Examiner—Vivian Garner
Attorney, Agent, or Firm—F. Wesley Turner; Joseph T. Cohen; Jerome C. Squillaro

[57] ABSTRACT

A process comprising (1) hydroformylation of allyl acetate or 1-propenyl acetate to form isomeric acetoxybutyraldehydes, and (2) recycle of the mixture obtained by dehydroformylation of at least a portion of the acetoxybutyraldehyde isomers as feedstock in (1).

3 Claims, No Drawings

PROCESS FOR HYDROFORMYLATION OF ALLYL ACETATE OR 1-PROPENYL ACETATE

This is a division of copending application Ser. No. 548,216, filed Feb. 10, 1975, now U.S. Pat. No. 3,941,851, which is a division of Ser. No. 371,929, filed June 20, 1973 now U.S. Pat. No. 3,880,913, issued Apr. 29, 1975.

BACKGROUND OF THE INVENTION

1. Field of the Invention

This invention provides a process for producing allyl acetate, 1-propenyl acetate or mixtures thereof by dehydroformylating 4-acetoxybutyraldehyde, 2-acetoxybutyraldehyde, 3-acetoxy-2-methylpropionaldehyde or mixtures thereof. This invention also provides an improved process for hydroformylating these products to 4-acetoxybutyraldehyde and an improved process for making 1,4-butanediol from propylene, acetic acid and oxygen.

2. Description of the Prior Art.

In my copending application A, Ser. No. 365,228 filed May 30, 1973 now abandoned, and assigned to the same assignee as the present invention, I have disclosed and claimed a process for making butanediols by oxidatively coupling propylene and acetic acid to produce allyl acetate which is then hydroformylated to produce the mixture of three isomeric acetoxybutyraldehydes. Hydrogenation of the mixture produces a mixture of isomeric acetoxybutanols which can also contain some of the diesters and free diols. In my copending application B, Ser. No. 365,231, filed May 30, 1973 now abandoned, and assigned to the same assignee as the present invention, I have disclosed and claimed a process wherein the hydrogenation is accomplished during the hydroformylation reaction. De-esterification of the acetoxybutanol mixture produces the desired butanediols which can be separated by distillation.

In my copending application C, Ser. No. 371,714, now abandoned, filed concurrently herewith and assigned to the same assignee as the present invention, I have disclosed and claimed that hydroformylation of 1-propenyl acetate under hydroformylating conditions in the presence of a cobalt hydroformylation catalyst yields essentially the same isomeric mixture of acetoxybutyraldehydes as is obtained from allyl acetate.

Prior to my discovery, the prior art, see for example J. Am. Chem. Soc. 70, 383 (1948) and 71, 3054 (1949), reported that the hydroformylation of allyl acetate led to only one product, 4-acetoxybutyraldehyde, in essentially a 70–75% yield. Although my work confirms this yield, I have also found that the balance of the allyl acetate has been converted to two isomers of the 4-acetoxybutyraldehyde, specifically, 2-acetoxybutyraldehyde and 3-acetoxy-2-methylpropionaldehyde in approximately equimolar amounts.

Although, as shown in my copending applications A and B referred to above, these two isomers can be converted to their corresponding butanediols, specifically 1,2-butanediol and 2-methyl-1,3-propanediol, neither of these two products are as desirable as 1,4-butanediol, which forms polyesters with dicarboxylic acids, such as terephthalic acid, which are commercially much more desirable than the polyesters obtained from the other two isomers. It would be highly desirable, therefore, to be able to obtain higher yields of the 4-acetoxybutyraldehyde either by decreasing the production of the other two isomers or by converting the latter into the desired isomer.

Insofar as I am aware, the only attempt to recycle an undesirable by-product of a hydroformylation reaction is described in British patent 1,241,646, its corresponding counterparts in other foreign countries, and in articles written by the inventors and coworkers, see for example, Angew. Chem., Internat. Edit. 9, 169 (1970) and 11, 155 (1972), Ind. Eng. Chem. 62 [4] 33 (1970). These references describe that in the hydroformylation of propylene to n-butyraldehyde, isobutyraldehyde is obtained as a less desired product. This latter product is dehydroformylated to propylene, carbon monoxide and hydrogen which can then be recycled in the hydroformylation reaction to increase the yield of the n-butyraldehyde in the over-all reaction. Other related art in this area teaches the production of saturated aliphatic compounds arising from the hydrogen interaction with the dehydroformylation product to hydrogenate the olefinic double bond. This latter reaction is called decarbonylation because, in effect, only carbon monoxide is removed from the starting product.

One of the convenient means for converting a compound containing an alcoholic hydroxyl group to an olefin is to make the acetate ester of the compound which is then thermolyzed or pyrolyzed to produce the olefin and acetic acid. For convenience, this ester thermolysis reaction, as applied to acetate esters, will be called dehydroacetoxylation since a hydrogen is removed from one carbon atom and the acetoxy group from the adjacent carbon atom to form acetic acid and create an olefinic double bond in the initial compound. Since the isomeric acetoxybutyraldehydes, to which this invention is directed, are acetate esters as well as aldehydes, they could undergo (a) the dehydroacetoxylation reaction to produce unsaturated aldehydes, (b) both the dehydroacetoxylation reaction and the hydrogenation reaction to produce saturated aldehydes, (c) the dehydroformylation reaction to produce unsaturated esters, (d) the dehydroformylation and hydrogenation reaction to produce saturated esters or (e) any combination of (a) through (d). It was indeed surprising to find that the dehydroformylation reaction could be effected with the other reactions occurring to a minimal extent.

SUMMARY OF THE INVENTION

I have found an indirect method of converting the two isomers, 2-acetoxybutyraldehyde and 3-acetoxy-2-methylpropionylaldehyde, to 4-acetoxybutyraldehyde. In the presence of a Group VIII noble metal catalyst, any one of these three isomers or a mixture containing any two or all three of them can be dehydroformylated at a temperature in the range of 120°–250° C. in a nonoxidizing atmosphere and in the presence of an essentially neutral noble metal catalyst to produce allyl acetate, 1-propenyl acetate or mixtures thereof. Dehydroformylation of these isomers leads to allyl acetate from 4-acetoxybutyraldehyde, 1-propenyl acetate from 2-acetoxybutyraldehyde and a mixture of allyl acetate, 1-propenyl acetate and variable amounts methacrolein and acetic acid from the less thermally stable 3-acetoxy-2-methylpropionaldehyde.

The amount of the methacrolein and acetic acid produced is dependent on the activity of the catalyst and the temperature used. Of the noble metal catalysts, those from platinum, rhodium and palladium are more active than the other Group VIII noble metals for promoting the dehydroformylation reaction. Platinum causes more hydrogenation of the desired unsaturated esters to saturated esters. Rhodium is satisfactory but much more expensive than palladium which is the preferred catalyst when it is desired to minimize the amount of unsaturated aldehyde or saturated ester by-products.

As I have disclosed in my above-referenced copending application C, 1-propenyl acetate can be hydroformylated to give the same three isomeric acetoxybutyraldehydes in essentially the same proportion as is obtained upon hydroformylation of allyl acetate. Therefore, the significance of my discovery of the dehydroformylation reaction described above is that, by separating some or all of the 4-acetoxybutyraldehyde from the balance of the mixture containing the other two isomers, the latter can be dehydroformylated to furnish feedstock for the hydroformylation reaction. By always recycling the two undesired isomers in this matter, the feedstock of the hydroformylation reactions, in effect, is all converted essentially to the desired 4-acetoxybutyraldehyde, which can then be readily hydrogenated to produce 4-acetoxy-1-butanol, which, in turn, can be de-esterified to produce 1,4-butanediol.

Not only has my discovery of this dehydroformylation reaction provided a process useful in itself for utilizing the isomeric acetoxybutyraldehydes, made by any other processes, but has also provided improvements in the hydroformylation reaction to increase the yield of 4-acetoxybutyraldehyde in the process described in my above-referenced copending application A for making butanediols from propylene, acetic acid and oxygen wherein the hydroformylation reaction is an important intermediate step. By being able to convert all of the hydroformylated products to 4-acetoxybutyraldehyde, the butanediol will all be the desired 1,4-butanediol.

DETAILS OF THE INVENTION

The dehydroformylation reaction can be carried out as a liquid phase, vapor phase or liquid-vapor phase reaction. Since the products of the reaction are lower boiling than the feedstock, the liquid phase reaction can be carried out at atmospheric pressure at a temperature in the range from the boiling point of the lowest boiling of the dehydroformylated products up to the boiling point of the lowest boiling component of the feedstock. Both allyl acetate and 1-propenyl acetate, which has two isomeric forms, boil in the range of 100°–106° C. Therefore, the minimum temperature that the dehydroformylation reaction could be carried out at would be about 110° C. However, at this temperature, the rate of the dehydroformylation reaction is so slow that it is preferred to use temperatures of at least 120° C. and preferably 140° C.

The maximum temperature for the reaction is determined by the lowest boiling component present in liquid phase. The lowest boiling isomer which would be present in the feedstock is 2-acetoxybutyraldehyde which has a boiling point of 168° C. which represents, therefore, the maximum temperature that can be used for the dehydroformylation reaction when carried out in the liquid phase at atmospheric pressure when this component is present and as long as it remains unreacted. When it is dehydroformylated any remaining isomers can be dehydroformylated at higher temperatures up to their boiling point. Higher temperatures can be obtained by increasing the pressure. Generally, however, it would be more desirable in this case to carry out the reaction either in the vapor phase or the liquid-vapor phase to save the expense of the more expensive equipment required when carrying out reactions under pressure.

When carrying out the reaction in the liquid phase, the noble metal catalyst with or without a support, but preferably having a large surface area, is suspended, generally with stirring in the feedstock. Since all the components of the feedstock are liquid, no solvent needs to be used. However, if desired, a solvent could be used but it generally should have a boiling point higher than any of the components of the feedstock and be nonreactive with either the components of the feedstock or the dehydroformylated products. Preferably, no solvent is used since the reaction is simplified.

The liquid phase reaction is carried out in a distillation apparatus which permits the dehydroformylated products to distill as they are formed. If desired, a fractionating column can be used to insure separation of any feedstock vapors from the vapors of the dehydroformylated products. In order to minimize side reactions, it is preferable to keep the residence time of the feedstock in the distillation apparatus to a minimum. This is most easily accomplished by maintaining a relatively small volume of the feedstock in contact with the catalyst in the boiler section and adding additional feedstock at a rate commensurate with the dehydroformylation reaction to maintain a relatively constant volume in the boiler of the distillation apparatus. Furthermore, by maintaining a high proportion of catalyst in contact with this volume in the boiler section, the rate of dehydroformylation reaction will be increased, thereby also decreasing the residence time of the feedstock in the boiler section. As will be readily apparent, an amount of catalyst should not be so great as to interfere with heat transfer or distillation of the liquid phase.

In carrying out the dehydroformylation reaction in the vapor phase at atmospheric pressure, it is self evident that the minimum temperature to be used would be governed by the highest boiling point of the components of the feedstock. Of the various isomeric acetoxybutyraldehydes to be dehydroformylated, the highest boiling is 4-acetoxybutyraldehyde which has a boiling point of 190° C. This means that in carrying out the dehydroformylation reaction in the vapor phase at atmospheric pressure, the temperature should be at least 190° C. Lower temperatures than this can be used by carrying out the vapor phase reaction at subatmospheric pressure. However, generally, there is no incentive to do this since at the lower temperatures, the reaction might just as well be carried out in the liquid phase rather than the vapor phase.

In carrying out the vapor phase reaction, the vapors of the feedstock, produced preferably in a flashtype distillation apparatus, are introduced to the reactor containing the noble metal catalyst at the desired temperature. To aid in the transport of the vapors from the distillation apparatus to the catalyst bed, an inert gas, such as nitrogen or a mixture of carbon monoxide and hydrogen is used as a carrier gas to sweep the vapors of the feedstock from the distillation apparatus into the heated tube containing the noble metal catalyst. The vapors issuing from the reactor are then condensed and separated, generally by distillation into their various components.

For the vapor phase reaction, the noble metal catalyst is preferably deposited on a neutral support which should, like the noble metal, have a large surface area. The support should be of such a granular size as to permit the vapors of the reactants and products to readily pass through without the particles themselves being swept from the reactor. Porous carbon pellets of 4–14 mesh size are an ideal support on which the noble metal is carried. In choosing the temperature to use, one must balance the degree of conversion against the yield of desired product. Generally, it is better to use the lower temperature and increase the vapor contact time with the catalyst bed or to increase the amount of catalyst deposited on the support rather than to increase the reaction temperature. Too high a reaction temperature leads to breakdown of the feedstock into noncondensable products in addition to the carbon monoxide and hydrogen generated by the dehydroformylation reaction. Should one encounter large yields of noncondensable gases over and above that generated by the carbon monoxide in the hydrogen, one should then decrease the temperature at which the dehydroformylation reaction is being performed. Such techniques are well-known to those skilled in the art and would be readily ascertained.

In carrying out the dehydroformylation reaction under liquid-vapor phase conditions, the liquid feed product is introduced to the catalyst bed at a temperature sufficiently high that the feedstock is converted to the vapor on contact with the catalyst bed. Because of the cooling effect resulting from the vaporization of the liquid feed, the catalyst bed is generally kept at a temperature higher than would normally be used for the vapor phase reaction in order that the cooling effect will be compensated for and the reaction be carried out at the temperature which would normally be used for the vapor phase reaction. Generally in carrying out this type of reaction, an inert carrier gas is also provided to insure carrying the vapors through the catalyst bed to the exit port where they are condensed and again separated as discussed above for the vapor phase reaction.

In carrying out the dehydroformylation of the isomeric acetoxybutyraldehydes by any of the above techniques, the particular conditions and catalysts selected are dependent on the particular isomers or mixtures of isomers to be dehydroformylated. Both 4-acetoxybutyraldehyde and 2-acetoxybutyraldehyde are much more thermally stable than the 3-acetoxy-2-methylpropionaldehyde. The first two isomers are easier to dehydroformylate than the third isomer. Both 4-acetoxybutyraldehyde (boiling point 190°, 90°/20 mm.) and 2-acetoxybutyraldehyde (boiling point 168°, 70°/20 mm.) can be readily distilled in an inert atmosphere at atmospheric pressure with no detectable dehydroacetoxylation to the corresponding olefinic aldehyde. In contrast, 3-acetoxy-2-methylpropionaldehyde (boiling point ca. 180°, ca. 80°/20 mm.) will always dehydroacetoxylate to produce significant quantities of methacrolein and acetic acid when distilled under atmospheric pressure. The degree to which this dehydroacetoxylation reaction occurs is dependent on the residence time in the distillation boiler at the distillation temperature.

Neither the allyl acetate nor the 1-propenyl acetate which are the products of the dehydroformylation of these isomeric acetoxybutyraldehydes will dehydroacetoxylate. Therefore, if 3-acetoxy-2-methylpropionaldehyde is to be dehydroformylated either neat or as an ingredient in the mixture with the other two isomers, the dehydroacetoxylation reaction can be minimized and the yield of dehydroformylated product maximized by choosing those reaction conditions and catalysts which cause the highest rate for the dehydroformylation reaction. Since this reaction does not occur in the absence of the noble metal catalyst, it is desirable to choose those reaction conditions which minimize both the time this isomer is at an elevated temperature and its contact time with the catalyst bed. Also it is desirable to have the catalyst be the most active catalyst and in its most active form so that the dehydroformylation reaction is completed in as short time as possible. As pointed out above, palladium would be the catalyst to use. To make it in its most active form, it should have as high surface area as possible and preferably be on an essentially neutral, porous catalyst support having a large surface area.

In addition to the hydrogenation and dehydroacetoxylation reactions discussed above, aldol type condensations, oxidation and carbonization reactions can also occur. The aldol condensation reactions can be controlled by maintaining essentially neutral conditions in the dehydroformylation reaction. This means that the acetoxybutyraldehyde feedstock should be free of any acids or bases and that the catalyst and its supports, if used, should likewise be essentially neutal. It, of course, is recognized that when 3-acetoxy-2-methylpropionaldehyde is one of the reactants that the dehydroacetoxylation reaction cannot be completely prevented and therefore the products issuing from the dehydroformylation reactor would contain some acetic acid. However, at this point in the reaction, there is little if any unconverted acetoxybutyraldehyde isomers left unreacted unless the contact time with the catalyst bed at the particular temperature has been insufficient to provide high yields of the dehydroformylated products.

Oxidation is easily controlled by using an inert atmosphere which excludes oxygen. Since both carbon monoxide and hydrogen will be products of the dehydroformylation reaction and it would be desirable to reuse this in a further hydroformylation reaction, it is preferred that the inert atmosphere be of carbon monoxide and hydrogen. However, in this case, reaction conditions should be chosen which will minimize hydrogenation of the olefinic compounds to saturated compounds. If desired, in starting up a reaction, other inert gases, for example nitrogen, can be used to initially establish an inert atmosphere which is then permitted to be replaced by the carbon monoxide and hydrogen atmosphere generated by the dehydroformylation reaction. The carbonization reaction is best controlled by insuring that no overheating occurs on the catalyst bed and that the temperature not exceed the temperature at which the desired rate of the dehydroformylation reaction occurs. This can readily be determined by monitoring the temperature throughout the length of the catalyst bed to detect runaway conditions and/or by the amount of uncondensible gases exiting from the reactor. Generally, the lowest temperature that can be used and yet attain the desired rate of dehydroformylation is desirable in order to attain the highest conversion rate with minimum by-product formation.

Not only does the activity of a particular catalyst depend upon its method of preparation but once prepared on its past history. As it is continued to be used, it will naturally lose some of its activity, but the desired reaction rate can be maintained by increasing the reaction bed temperature or by regenerating the catalyst by art recognized techniques. Within the above parameters, the temperature which I have found most satisfactory is in the range of 125°–250° C., preferably 140°–220° C. When only 4-acetoxybutyraldehyde, 2-acetoxybutyraldehyde or mixtures of these two isomers are to be dehydroformylated, their thermal stability permits slower reaction rate and catalyst of lower activity to be used than when the 3-acetoxy-2-methylpropionaldehyde isomer is present.

In preparing the noble metal catalyst, any of the well-known techniques known in the art can be used. A salt of the noble metal can be precipitated as the hydroxide or oxide which can then either by prereduced in a reducing atmosphere or reduced on the initial introduction of the aldehyde isomers to be dehydroformylated. To prepare the supported catalyst, a porous neutral support, i.e. one having neither an acidic nor basic reaction, for example carbon black, can be impregnated in the usual way with a soluble noble metal salt which is then reduced in the same way as described above for the noble metal oxide or hydroxide.

As more fully detailed in my above referenced copending applications, hydroformylation of allyl acetate, 1-propenyl acetate or mixtures thereof under hydroformylating conditions in the presence of a cobalt hydroformylating catalyst leads to a mixture of 4-acetoxybutyraldehyde, as the predominant product, and its two isomers 2-acetoxybutyraldehyde and 3-acetoxy-2-methylpropionaldehyde. Hydrogenation of this isomeric mixture leads to a mixture comprising the mono-acetate esters of 1,4-butanediol, 1,2-butanediol and 2-methyl-1,3-propanediol, respectively. Some transesterification can occur during the hydrogenation reaction so that the mixture also can contain some of the diacetates of these butanediols as well as some of the free butanediols. However, during the de-esterification process under de-esterification conditions, all of the esters are converted to the free butanediols so that the degree to which the transesterification reaction has occurred presents no processing problem. Of the three butanediols produced, the most commercially important one is 1,4-butanediol which forms polyesters with dicarboxylic acids such as terephthalic acid, which are commercially much more desirable than polyesters obtained from the other two isomers. Since this butanediol is the result of the hydrogenation and de-esterification of the 4-acetoxybutyraldehyde, it is obvious that the 4-acetoxybutyraldehyde is a much more desirable product of the hydroformylation reaction.

The mixture of the isomeric butyraldehydes produced in the above-described hydroformylation reaction could be readily separated by fractional distillation into the three components if it were not for the thermal instability of the 3-acetoxy-2-methylpropionaldehyde. However, I have found that by flash distillation at a temperature above that of the two lowest boiling isomers, 2-acetoxybutyraldehyde and 3-acetoxy-2-methylpropionaldehyde respectively, that these two isomers can be distilled leaving substantially pure 4-acetoxybutyraldehyde in the still pot. The amount of 4-acetoxybutyraldehyde which also codistills is dependent on the actual maximum temperature used in the flash distillation. The still pot residue can then be fractionally distilled to produce very pure 4-acetoxybutyraldehyde which can then be hydrogenated to 4-acetoxy-1-butanol using any of the well-known hydrogenation catalysts and hydrogenation conditions to produce substantially pure 4-acetoxy-1-butanol. This latter product can be readily de-esterified using any of the well-known de-esterification processes to produce 1,4-butanediol and acetic acid. The acetic acid can be recycled to make allyl acetate by oxidatively coupling propylene with acetic acid.

The mixture of isomers resulting from the above-described flash distillation (to which may be added, if desired, any of the isomeric mixtures removed in the fractional distillation to further purify the 4-acetoxybutyraldehyde as described above), may then be subjected to the above described dehydroformylation procedure to produce a mixture of allyl acetate and 1-propenyl acetate which may also contain some acetic acid and methacrolein as described above. After the removal of these latter two by-products, the mixture of the allyl acetate and 1-propenyl acetate can be hydroformylated as described in my copending application C referenced above to again produce a mixture of the isomeric acetoxybutyraldehydes in which the 4-acetoxybutyraldehyde predominates. It is therefore seen that this process of removing some of the 4-acetoxybutyraldehyde from the mixture containing the other two isomers and dehydroformylating the latter to produce feedstock for the hydroformylation reaction, effectively recycles the undesired isomers. The combination of this dehydroformylation reaction with the hydroformylation reaction represents an improvement in the latter reaction since it results in more of the feedstock being converted to the 4-acetoxybutyraldehyde. The higher yield of this isomer also results in a higher yield of 1,4-butanediol.

In carrying out the hydroformylation of the mixture of allyl acetate and 1-propenyl acetate obtained by the process of this invention, I can use any of the procedures disclosed in my copending application C hereby incorporated by reference. In carrying out the overall process whereby (a) propylene is oxidatively coupled with acetic acid to form allyl acetate, (b) the allyl acetate, 1-propenyl acetate, or mixture of allyl acetate and 1-propenyl acetate is hydroformylated to produce the isomeric acetoxybutyraldehydes, which are (c) treated according to the process of this invention to produce substantially pure 4-acetoxybutyraldehyde, which is (d) hydrogenated to produce 4-acetoxy-1-butanol, which is (e) de-esterified to produce 1,4-butanediol and acetic acid in a form which can be recycled to be oxidatively coupled with propylene, I may use any of the procedures for the oxidative coupling, hydroformylation, hydrogenation and the de-esterification disclosed in my copending application A cross-referenced above and hereby incorporated by reference.

DESCRIPTION OF PREFERRED EMBODIMENTS

In order that those skilled in the art may better understand my invention, the following examples are given by way of illustration and not by way of limitation. Temperatures are given in degrees Centigrade and pressures are reported in pounds per square inch gauge.

Examples 1–4 illustrate carrying out the dehydroformylation reaction in the liquid phase.

EXAMPLE 1

2-Acetoxybutyraldehyde was prepared essentially free of its isomers by hydroformylation of 1-propenyl acetate using rhodium bis(triphenylphosphine) carbonyl chloride [RhCl(CO)$_2$(PPh$_3$)$_2$] as the catalyst. A suspension of 1.0 gram of 10% palladium on carbon black (freshly activated under hydrogen) in 6.4 grams of the 2-acetoxybutyraldehyde was heated at 155°–190° for 2 hours, with an insulated 100 mm. Vigreaux column and condenser mounted directly above the reaction vessel. The distillate collected in that period was 4.6 grams of pale yellow liquid boiling in the 85°–103° range. (Gas was also evolved.) Quantitative VPC analysis (propionic acid internal standard) showed the presence of 2.9 grams of 1-propenyl acetate (59% yield, trans : cis ratio about 3:1), 0.92 gram of propyl acetate (18%), 0.72 gram of acetic acid (24%), and about 0.04 gram of unidentified lower boiling substrates. No allyl acetate was detected.

EXAMPLE 2

4-Acetoxybutyraldehyde was prepared by the dicobalt octacarbonyl-catalyzed hydroformylation of allyl acetate and isolated from its isomeric by-products by repeated distillation. A suspension of 1.0 gram of 10% palladium on acetylene black in 10.0 grams of 4-acetoxybutyraldehyde was heated at 140°–180° for one hour as in Example 1. Gas was evolved, and 6.1 grams of pale yellow liquid was collected at 80°–106°. Quantitative VPC analysis showed the presence of 2.1 grams of allyl acetate (27% yield), 0.94 gram of propyl acetate (12%), and 1.9 grams of acetic acid (41%). No 1-propenyl acetate was detected.

EXAMPLE 3

A suspension of 1.0 gram of 5% platinum on carbon (activated under hydrogen) in 4.1 grams of 2-acetoxybutyraldehyde was heated at 155°–180° for 4 hours. Collected as in the above examples was 1.2 grams of distillate boiling over the 88°–102° range. Analysis by VPC and NMR showed the presence of 0.45 gram of 1-propenyl acetate (14% yield, trans : cis ratio about 2:1), about 0.1 gram of propyl acetate (3%), and about 0.5 gram of acetic acid (26%). A large amount of starting aldehyde remained unconverted in the still pot.

EXAMPLE 4

A suspension of 1.0 gram of 5% rhodium on carbon in 10.0 grams of 2-acetoxybutyraldehyde was heated at 145°–180° for 2 hours. Gas was evolved. Collected as in the above cases was 5.2 grams of distillate which boiled in the 80°–108° range. VPC analysis showed the presence of 2.8 grams of 1-propenyl acetate (36% yield, trans : cis ratio about 3:1), 0.8 gram of propyl acetate (10%), and 1.2 grams of acetic acid (26%).

Examples 5–8 illustrate one method of carrying out the dehyroformylation reaction in the liquid-vapor phase.

Since the feedstock immediately volatilized from the catalyst bed in these examples, the actual reaction temperature is probably nearer that of the boiling point of the feedstock than it is that of the catalyst bed temperature.

EXAMPLE 5

A 5.0 gram bed of 10% palladium on carbon was heated at about 300° and activated under hydrogen. After the hydrogen atmosphere was replaced with nitrogen, a mixture of 11.6 grams of 2-acetoxybutyraldehyde, 3.2 grams of 3-acetoxy-2-methylpropionaldehyde, 4.4 grams of 4-acetoxybutyraldehyde and 0.8 gram of acetic acid was dropped slowly (over 30 minutes) onto the hot catalyst. An insulated 100 mm. Vigreaux column and condenser were mounted directly above the reaction vessel. Gas was evolved. The distillate, 13.4 grams collected at 60°–110° in 1 hour total reaction time contained, as found by VPC and NMR analysis, 4.1 grams of 1-propenyl acetate (46% yield based on 2-acetoxybutyraldehyde, 27% yield based on all aldehydes), 1.8 grams of allyl acetate (53% yield based on 4-acetoxybutyraldehyde, 12% yield based on all aldehydes), and 2.3 grams of propyl acetate (15% yield based on all aldehydes). The other products were acetic acid and methacrolein.

EXAMPLE 6

The aldehyde mixture described in Example 5, 10.0 grams, was dropped onto a bed of 3.1 grams of 5% rhodium on carbon maintained at about 300°. As in the previous case, gas was evolved and distillate was collected (5.1 grams boiling over the 58°–108° range). Produced, as shown by VPC and NMR analysis, were 1.6 grams of 1-propenyl acetate (36% yield based on 2-acetoxybutyraldehyde, 21% yield based on all aldehydes), 0.55 gram of allyl acetate (32% yield based on 4-acetoxybutyraldehyde, 7% yield based on all aldehydes), and 0.7 gram of propyl acetate (9% yield based on all aldehydes). The other products were acetic acid and methacrolein.

EXAMPLE 7 the aldehyde mixture described in Example 5, 10.0 grams, was dropped onto a bed of 3.0 grams of 5% platinum on carbon maintained at about 300°. As in the previous cases, gas was evolved and distillate was collected (6.2 grams boiling over the 56°–104° range). Produced, as found by VPC and NMR analysis, were 1.0 gram of 1-propenyl acetate (22% yield based on 2-acetoxybutyraldehyde, 13% yield based on all aldehydes), 0.3 gram of allyl acetate (18% yield based on 4-acetoxybutyraldehyde, 4% yield based on all aldehydes), and 1.1 grams of propyl acetate (14% yield based on all aldehydes). The other products were acetic acid and methacrolein.

EXAMPLE 8

The aldehyde mixture described in Example 5, 10.0 grams, was dropped onto a bed of 4.1 grams of 5% ruthenium on carbon maintained at about 300°. As in the previous cases, gas was evolved and distillate was collected (5.2 grams boiling over the 60°–110° range). Produced as shown by VPC and NMR analysis, were 0.6 gram of 1-propenyl acetate (13% yield based on 2-acetoxybutyraldehyde, 8% yield based on all aldehydes), 0.3 gram of allyl acetate (18% yield based on 4-acetoxybutyraldehyde, 4% yield based on all aldehydes), and 0.8 gram of propyl acetate (10% yield based on all aldehydes).

The yield of methacrolein in Examples 5–8 increased as the total yield of aldehyde reversion products decreased.

EXAMPLE 9

A heavy wall 16 mm. I.D. × 70 cm. effective length glass tube was charged with 22 grams of 0.2% palladium on 6–14 mesh carbon and heated at 200°–220°. Then 25.0 grams of the aldehyde mixture described in Example 5 was evaporated and passed through the tube with a slow nitrogen carrier stream over 30 minutes. A pale yellow liquid (12.4 grams) was condensed and collected. As found by VPC and NMR analysis, it contained about 3 grams of 1-propenyl acetate, about one gram of allyl acetate, and about 0.5 gram of propyl acetate. The other materials were acetic acid, methacrolein and the aldehyde starting materials (about 20% unconverted).

The above examples have clearly demonstrated the best mode known to me of carrying the various aspects of my invention into effect. As will be readily understood by those skilled in the art, variations can be made in practicing my invention as clearly taught in the balance of the specification, by the cross-referenced applications and by the prior art on conversion of alkenes to unsaturated esters, hydroformylation, hydrogenation and de-esterification without departing from the true intended scope of my invention.

My invention can be used as an independent process for conversion of any one or a mixture of any of the isomeric acetoxybutyraldehydes to produce the olefinic unsaturated esters which are useful in and of themselves. In this respect, the dehydroformylation of 2-acetoxybutyraldehyde can be used as an alternative process of producing 1-propenyl acetate for the present process disclosed in the art. Allyl acetate has a wide variety of uses as the literature on this compound will show. It has already been discussed and shown above how my process can be used to provide an improvement in other known processes, specifically the hydroformylation process and the process for making 1,4-butanediol from propylene and acetic acid. Where desired, advantage can be taken of the thermal instability of the 3-acetoxy-2-methylpropionaldehyde to eliminate it from a mixture with one or more of its isomers by heating the mixture and distilling the methacrolein and acetic acid as the one formed. The acetic acid can be recycled to make allyl acetate from propylene. The remaining isomers can then be readily isolated and either hydrogenated to monoesters or dehydroformylated as described above. These and other modifications of this invention and its uses as will be readily discerned by those skilled in the art, based on the teachings of the prior art herein incorporated by reference and the specific teachings of this application, can be employed within the scope of the invention. The invention is intended to include all such modifications and variations as are embraced within the following claims.

I claim:

1. In the process of hydroformylating allyl acetate or a mixture of allyl acetate and 1-propenyl acetate under hydroformylating conditions in the presence of a cobalt hydroformylating catalyst to produce a mixture comprising 4-acetoxybutyraldehyde, as the predominant product, and its two isomers, 2-acetoxybutyraldehyde nd 3-acetoxy-2-methylpropionaldehyde, the improvement wherein at least some of the 4-acetoxybutyraldehyde is separated from the mixture containing its two isomers and the mixture containing the isomers is dehydroformylated at a temperature in the range of 120°–250° C. in a non-oxidizing atmosphere in the presence of a catalyst selected from the group consisting of a Group VIII noble metal and mixtures thereof or a Group VIII noble metal and mixtures thereof on an essentially neutral support to produce feedstock which is recycled to the hydroformylation step.

2. The process improvement of claim 1, wherein said mixture containing the isomers is dehydroformylated at a temperature in the range of 120°–250° C. in an atmosphere of CO and $H_2$ in the presence of palladium, rhodium or mixtures thereof supported on an essentially neutral support to produce feedstock which is recycled to the hydroformylation step.

3. The process improvement of claim 1, wherein the 4-acetoxybutyraldehyde is separated from said mixture containing its two isomers by flash distillation at a temperature above the boiling point of 2-acetoxybutyraldehyde and 3-acetoxy-2-methyl propionaldehyde.